(12) United States Patent
Kumazaki et al.

(10) Patent No.: US 10,359,356 B2
(45) Date of Patent: Jul. 23, 2019

(54) TOOL ABNORMALITY DETERMINATION SYSTEM

(71) Applicant: FUJI MACHINE MFG. CO., LTD., Chiryu-shi, Aichi (JP)

(72) Inventors: Shinya Kumazaki, Chiryu (JP); Kazuya Furukawa, Chiryu (JP)

(73) Assignee: FUJI MACHINE MFG. CO., LTD., Chiryu-shi (JP)

(*) Notice: Subject to any disclaimer, the term of this patent is extended or adjusted under 35 U.S.C. 154(b) by 436 days.

(21) Appl. No.: 14/189,564

(22) Filed: Feb. 25, 2014

(65) Prior Publication Data

US 2014/0257717 A1 Sep. 11, 2014

(30) Foreign Application Priority Data

Mar. 6, 2013 (JP) .................. 2013-043907

(51) Int. Cl.
| | | |
|---|---|---|
| G05B 19/4065 | (2006.01) | |
| B23Q 17/09 | (2006.01) | |
| G01N 19/08 | (2006.01) | |
| G01N 3/58 | (2006.01) | |

(52) U.S. Cl.
CPC ......... *G01N 19/08* (2013.01); *B23Q 17/0961* (2013.01); *G01N 3/58* (2013.01); *G05B 19/4065* (2013.01); *G05B 2219/34464* (2013.01); *G05B 2219/34465* (2013.01); *G05B 2219/37076* (2013.01); *G05B 2219/37342* (2013.01)

(58) Field of Classification Search
CPC ...... G05B 2219/37076; G05B 19/4065; G05B 2219/37342; G05B 2219/34464; G05B 2219/34465; B23Q 17/0961
See application file for complete search history.

(56) References Cited

U.S. PATENT DOCUMENTS

| | | | | |
|---|---|---|---|---|
| 5,521,474 | A | * 5/1996 | Hahn ................... | H02H 7/0851 318/266 |
| 2003/0163286 | A1 | * 8/2003 | Yasugi ............... | G05B 19/4065 702/185 |
| 2003/0167100 | A1 | * 9/2003 | Fujita ................. | G05B 19/4065 700/175 |
| 2008/0148827 | A1 | * 6/2008 | Keski-Hynnila ..... | G01M 15/05 73/114.31 |

(Continued)

FOREIGN PATENT DOCUMENTS

| | | |
|---|---|---|
| JP | A-7-132440 | 5/1995 |
| JP | A-2001-150244 | 6/2001 |
| JP | 2009-078338 A | 4/2009 |

OTHER PUBLICATIONS

Jan. 5, 2017 Office Action issued in Japanese Patent Application No. 2013-043907.

*Primary Examiner* — Jennifer E Simmons
(74) *Attorney, Agent, or Firm* — Oliff PLC

(57) ABSTRACT

A tool abnormality detection system corrects a monitoring range for a load on a tool in an $M^{th}$ cycle by using load data of at least one of $1^{st}$ to $(M-1)^{th}$ cycles (where M is an integer of 2 or more), wherein processing work on a single workpiece corresponds to a single cycle, and the load data is data about the load on the tool in the cycle.

7 Claims, 9 Drawing Sheets

(56) References Cited

U.S. PATENT DOCUMENTS

| | | | | |
|---|---|---|---|---|
| 2011/0320388 A1* | 12/2011 | Wong | ................ | G05B 23/0232 |
| | | | | 706/12 |
| 2012/0271587 A1* | 10/2012 | Shibuya | ............ | G05B 23/0229 |
| | | | | 702/127 |
| 2013/0097128 A1* | 4/2013 | Suzuki | ............... | G05B 23/0264 |
| | | | | 707/693 |

* cited by examiner

TOOL ABNORMALITY DETERMINATION SYSTEM

INCORPORATION BY REFERENCE

The disclosure of Japanese Patent Application No. 2013-043907 filed on Mar. 6, 2013 including the specification, drawings and abstract is incorporated herein by reference in its entirety.

BACKGROUND OF THE INVENTION

1. Field of the Invention

The present invention relates to tool abnormality determination systems that detect abnormalities of a tool such as chipping by monitoring a load during processing by a lathe, etc.

2. Description of Related Art

In a lathe, a load on a tool changes if the cutting edge of the tool is chipped during processing of a workpiece. Specifically, a current value and torque of a motor that moves the tool, and a current value and torque of a motor for a spindle that moves the workpiece fluctuate if the cutting edge of the tool is chipped during processing of the workpiece. The tool abnormality determination systems monitor the load on the tool based on such a change in load. That is, the tool abnormality determination systems compare an actual change in load on the tool with a monitoring range for load monitoring, and determine that there is an abnormality in the tool such as chipping, if the actual load is out of the monitoring range.

Japanese Patent Application Publication No. H07-132440 (JP H07-132440 A) discloses a processing load monitoring method in which sampling data of motor torque is obtained by performing test-cutting a plurality of times and a load monitoring threshold is set based on the sampling data.

In the processing load monitoring method of Japanese Patent Application Publication No. H07-132440 (JP H07-132440 A), however, the threshold or the monitoring range that has been set cannot be changed once processing of a workpiece is started.

Accordingly, if the state of the lathe during setting of the monitoring range is different from that of the lathe during actual processing of the workpiece (when the monitoring range is used), the load tends to be out of the monitoring range even through there is actually no abnormality in the tool.

That is, the state of the lathe before idling is different from that of the lathe after idling. In the state before idling (e.g., upon cold start), lubricant in each part of the lathe has a low temperature and thus has high viscosity, and a ball screw for slide drive has a low temperature. The ball screw therefore has a high preload, and a nut portion does not move smoothly. This reduces mechanical efficiency and thus increases the load on the motors.

On the other hand, in the state after idling, the lubricant in each part of the lathe has a high temperature and thus has low viscosity, and the ball screw for slide drive has a high temperature. The ball screw therefore has a low preload, and the nut portion moves smoothly. This increases mechanical efficiency and thus reduces the load on the motors.

As described above, in the processing load monitoring system method of JP H07-132440 A, sampling data of motor torque is obtained by performing test-cutting a plurality of times, and a load monitoring threshold is set based on the sampling data. Accordingly, if the threshold is set based on the motor torque before idling of the lathe, the load tends to be smaller than the threshold when a workpiece is actually processed after idling.

On the other hand, if the threshold is set based on the motor torque after idling of the lathe, the load tends to be larger than the threshold when the workpiece is actually processed before idling (e.g., the morning after the day the threshold was set).

In the processing load monitoring method of JP H07-132440 A, if the state of the lathe during setting of the monitoring range is different from that of the lathe during actual processing of the workpiece (when the monitoring range is used), the load thus tends to be out of the monitoring range even through there is actually no abnormality in the tool.

Japanese Patent Application Publication No. 2001-150244 (JP 2001-150244 A) also discloses a method of setting a reference value before the start of operation of a gear shaper and permanently storing the reference value (e.g., claim 10 of JP 2001-150244 A), as in the processing load monitoring method of JP H07-132440 A.

SUMMARY OF THE INVENTION

It is an object of the present invention to provide a tool abnormality determination system capable of accurately detecting an abnormality in a tool according to the state of a machine tool.

(1) In order to solve the above problem, a tool abnormality determination system of the present invention corrects a monitoring range for a load on a tool in an $M^{th}$ cycle by using load data of at least one of $1^{st}$ to $(M-1)^{th}$ cycles (where M is an integer of 2 or more), wherein processing work on a single workpiece corresponds to a single cycle, and the load data is data about the load on the tool in the cycle.

According to the tool abnormality determination system of the present invention, the monitoring range of the $M^{th}$ cycle can be corrected by using the load data of (at least one of) the $1^{st}$ to $(M-1)^{th}$ cycles (where M is an integer of 2 or more). The monitoring range can thus be corrected according to a change in mechanical efficiency of a machine tool for which the tool abnormality determination system is used. Abnormalities in the tool can therefore be accurately detected regardless of when the monitoring range is set (e.g., before or after idling).

(2) In the configuration of (1), the cycle may include an air-cut step of moving the tool so as to bring the tool into contact with the workpiece, and an actual processing step of processing the workpiece by using the tool, the actual processing step may be performed after the air-cut step, a plurality of pieces of the load data which are detected in or before the air-cut step in the $M^{th}$ cycle may have early-stage data including at least one piece of the load data, and later-stage data including at least one piece of the load data which is detected later than the load data detected last in the early-stage data, and the monitoring range in the actual processing step of the $M^{th}$ cycle may be corrected by using a load ratio regarding a ratio between the early-stage data and the later-stage data.

The expression "in or before the air-cut step in the $M^{th}$ cycle" includes the air-cut step in the $M^{th}$ cycle. The early-stage data and the later-stage data may partially overlap each other in time. The early-stage data and the later-stage data may be detected in different steps from each other, or may be detected in the same step.

According to this configuration, the monitoring range can be corrected by using the load ratio (e.g., (the average value of the load data included in the early-stage data)/(the average value of the load data included in the later-stage data)).

(3) In the configuration of (2), a production method of the workpiece may include a teaching process which includes at least one of the cycles, and in which the monitoring range is set by using the load data detected in the cycle, and a processing process which includes at least one of the cycles, and in which the workpiece is processed while monitoring the load on the tool by using the monitoring range, and the early-stage data may be detected in the cycle of the teaching process.

The production method of the workpiece includes the teaching process and the processing process. In the teaching process, at least one of the cycles is performed (the cycle includes the air-cut step and the actual processing step). The load data is detected in the cycle. In the teaching process, the monitoring range is set based on the load data. In the processing step, the workpiece is processed by using the monitoring range set in the teaching process.

According to this configuration, the early-stage data is detected in the cycle of the teaching process. That is, the early-stage data for correcting the monitoring range is detected when the monitoring range is set. Thus, the state of the load at the time the monitoring range is set can be reflected in the load ratio.

(4) In the configuration of (3), the early-stage data may be detected in the air-cut step, and the later-stage data may be detected in the air-cut step in the cycle of the processing process.

The workpiece is processed in the actual processing step of the cycle. Accordingly, variation in shape, material, etc. among the workpieces tends to be reflected in the load data. According to this configuration, the early-stage data and the later-stage data are detected in the air-cut step of moving the tool. The variation among the workpieces is therefore less likely to be reflected in the load ratio.

(5) In the configuration of (3), the early-stage data may be detected in the actual processing step, and the later-stage data may be detected in the actual processing step in the cycle of the processing process.

According to this configuration, both the early-stage data and the later-stage data are detected in the actual processing step of processing the workpiece. The load ratio can therefore be set even if the period of the air-cut step is short.

(6) In the configuration of (5), the later-stage data may be detected in the actual processing step in the $(M-1)^{th}$ cycle. According to this configuration, this time's ($M^{th}$) monitoring range can be corrected by using the load data of the previous $((M-1)^{th})$ cycle.

(7) In the configuration of (5), the later-stage data may be detected in the actual processing steps in a plurality of the cycles including the $(M-1)^{th}$ cycle. According to this configuration, this time's ($M^{th}$) monitoring range can be corrected by using the load data of the plurality of cycles up to the previous $((M-1)^{th})$ cycle.

According to the present invention, a tool abnormality determination system can be provided which can accurately detect abnormalities in a tool according to the state of a machine tool.

DETAILED DESCRIPTION OF THE EMBODIMENTS

Figure 1:
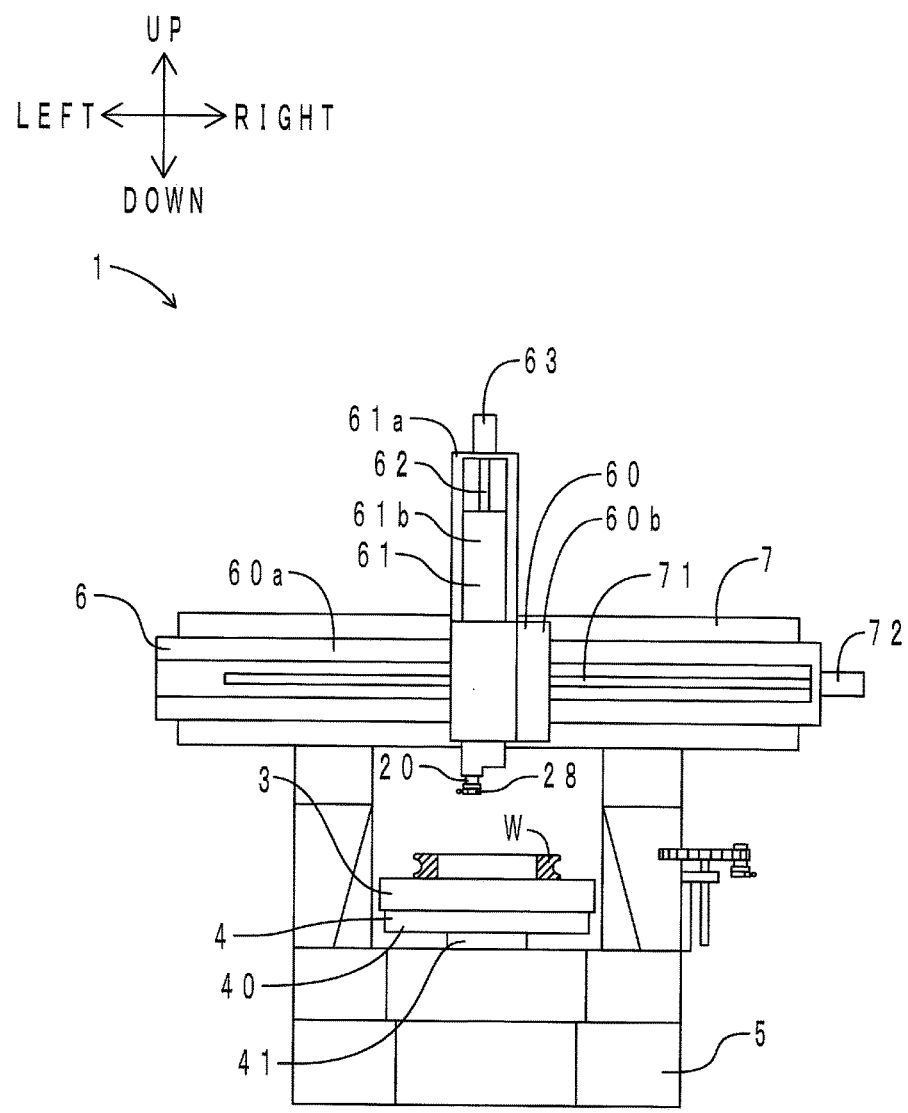
FIG. 1 is a front view of a lathe having a tool abnormality determination system according to an embodiment of the present invention.
Figure 2:
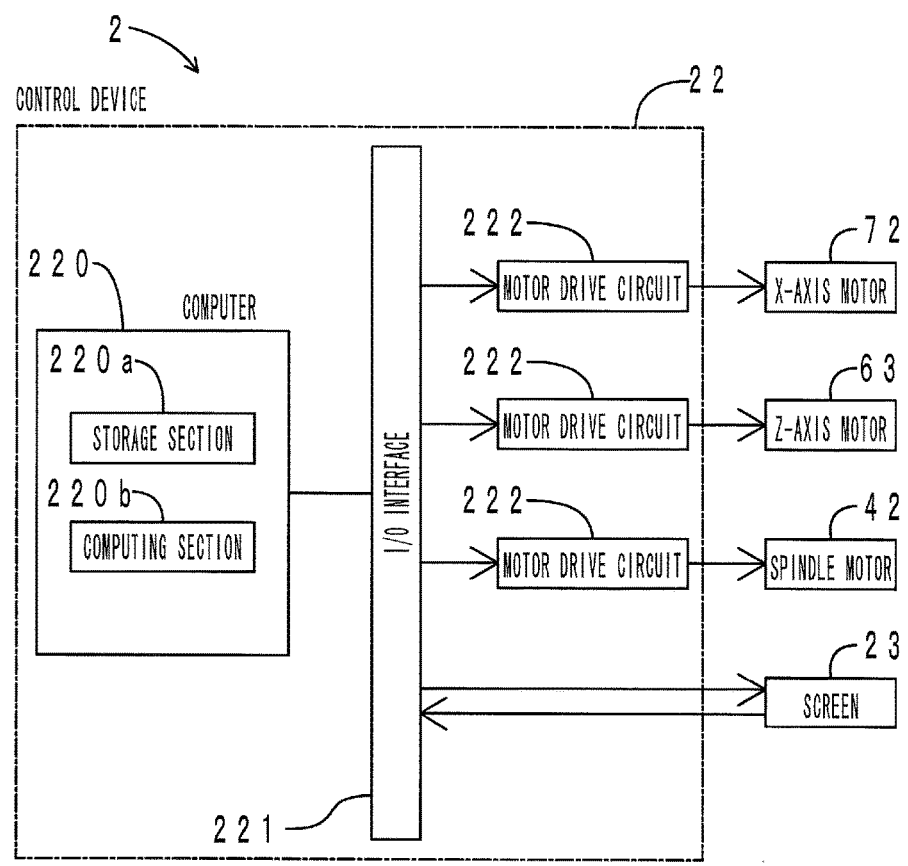
FIG. 2 is a block diagram of the lathe.

An embodiment of a tool abnormality determination system of the present invention will be described below.
(Configuration of Lathe)
First, the configuration of a lathe having a tool abnormality determination system of the present embodiment will be described. FIG. 1 is a front view of the lathe having the tool abnormality determination system of the present embodiment. FIG. 2 is a block diagram of the lathe. As shown in FIGS. 1 and 2, a lathe 1 of the present embodiment includes a tool abnormality determination system 2, a chuck 3, a table 4, a bed 5, a slide portion 6, and a column 7.

[Chuck 3, Table 4, Bed 5, and Column 7]
The table 4 includes a table body 40 and a spindle 41. The spindle 41 is accommodated in the bed 5. The upper end of the spindle 41 protrudes from the upper surface of the front part of the bed 5. The table body 40 is fixed to the upper end of the spindle 41.

The chuck 3 is fixed to the upper surface of the table body 40. The chuck 3 is capable of fixing and releasing a workpiece W. The workpiece W, the chuck 3, and the table 4 are capable of rotating about an axis in a horizontal plane by a driving force that is transmitted from a spindle motor 42 to the spindle 41.

The column 7 is placed on the front upper part of the rear part of the bed 5, and includes a ball screw portion 71 and an X-axis motor 72. The ball screw portion 71 extends in the left-right direction. A drive shaft of the X-axis motor 72 is coupled to a shaft part of the ball screw portion 71.

[Slide Portion 6]
The slide portion 6 includes an X-axis slide portion 60, a Z-axis slide portion 61, a ball screw portion 62, and a Z-axis motor 63.

The X-axis slide portion 60 includes an X-axis slide guide 60a and an X-axis slide 60b. The X-axis slide guide 60a is fixed in front of the column 7, and extends in the left-right direction (corresponding to the X-axis direction). The X-axis slide 60b is capable of moving in the left-right direction with respect to the X-axis slide guide 60a. A nut part of the ball screw portion 62 is attached to the X-axis slide 60b. The driving force of the X-axis motor 72 is transmitted to the X-axis slide 60b via a shaft part and the nut part of the ball screw portion 62. That is, the X-axis slide 60*b* is capable of moving in the left-right direction by the driving force of the X-axis motor 72.

The Z-axis slide portion 61 includes a Z-axis slide guide 61*a* and a Z-axis slide 61*b*. The Z-axis slide guide 61*a* extends in the up-down direction (corresponding to the Z-axis direction). The Z-axis slide guide 61*a* is placed in front of the X-axis slide 60*b*. The Z-axis slide 61*b* is capable of moving in the up-down direction with respect to the Z-axis slide guide 61*a*.

The ball screw portion 62 extends in the up-down direction. The Z-axis motor 63 is placed on the upper end of the Z-axis slide guide 61*a*. A drive shaft of the Z-axis motor 63 is coupled to the shaft part of the ball screw portion 62. The nut part of the ball screw portion 62 is attached to the Z-axis slide 61*b*. The driving force of the Z-axis motor 63 is transmitted to the Z-axis slide 61*b* via the shaft part and the nut part of the ball screw portion 62. That is, the Z-axis slide 61*b* is capable of moving in the up-down direction by the driving force of the Z-axis motor 63.

[Tool Abnormality Determination System 2]

The tool abnormality determination system 2 includes a tool rest 20, a control device 22, a screen 23, and a tool bit 28. The tool bit 28 is included in the concept of the "tool" of the present invention.

The tool rest 20 is placed on the lower end of the Z-axis slide 61*b*. The tool bit 28 is replaceably attached to the tool rest 20. The workpiece W is cut with a blade at the tip end of the tool bit 28. The tool rest 20 and the tool bit 28 are driven in the up-down and left-right directions by the X-axis slide portion 60 and the Z-axis slide portion 61.

The control device 22 includes a computer 220, an input/output (I/O) interface 221, and a plurality of motor drive circuits 222. The computer 220 includes a storage section 220*a* and a computing section 220*b*. A monitoring range (a lower limit threshold, an upper limit threshold) described below is stored in the storage section 220*a*. The monitoring range can be updated and corrected. The I/O interface 221 is connected to the computer 220, and is also connected to the X-axis motor 72, the Z-axis motor 63, and the spindle motor 42 via the motor drive circuits 222. The I/O interface 221 is also connected to the screen 23.

(Tool Abnormality Determination Method)

Figure 3:
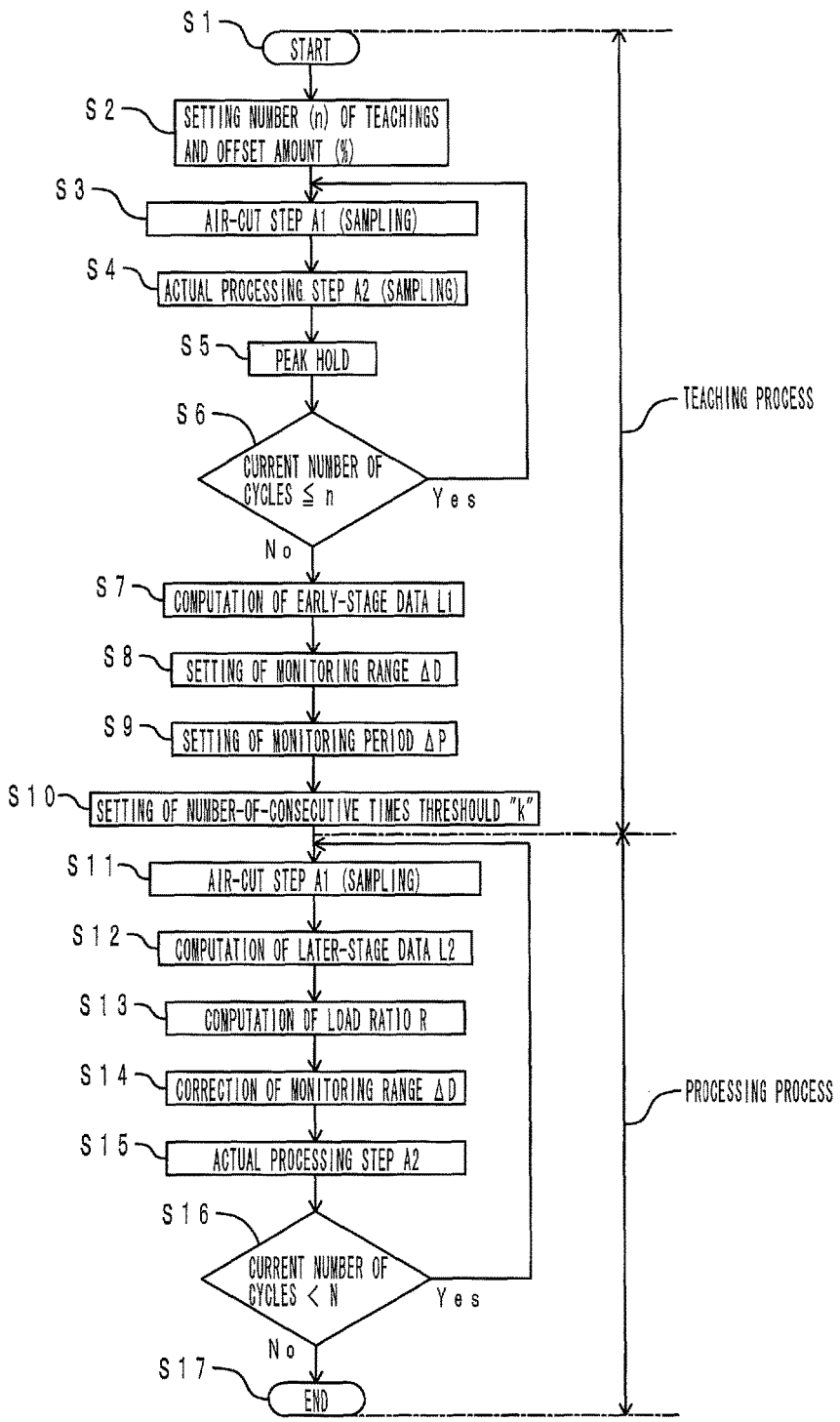
FIG. 3 is a flowchart of a tool abnormality determination method that is performed by using the tool abnormality determination system.
Figure 4:
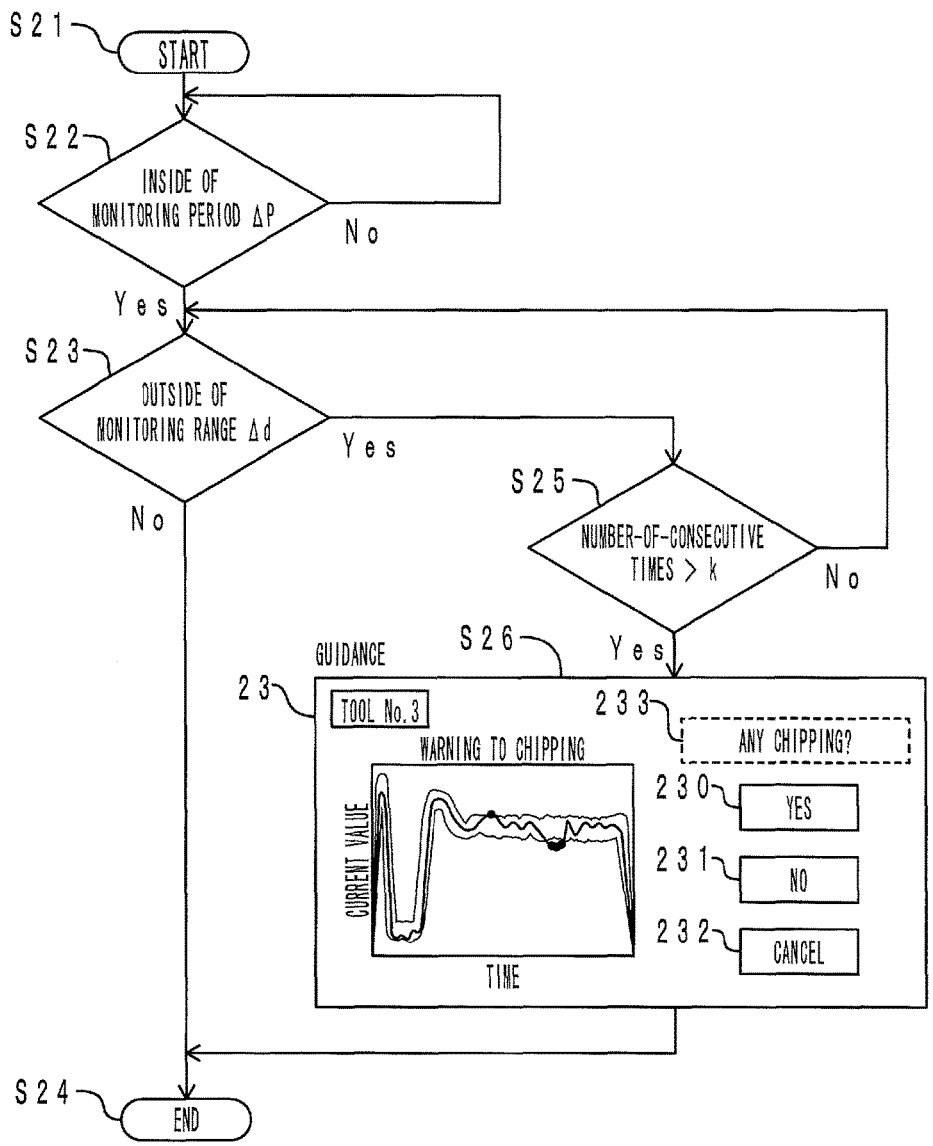
FIG. 4 is a flowchart of a monitoring range update step that is performed in an actual processing step of FIG. 3.

A tool abnormality determination method that is performed by using the tool abnormality determination system of the present embodiment will be described below. FIG. 3 is a flowchart of the tool abnormality determination method that is performed by using the tool abnormality determination system of the present embodiment. FIG. 4 is a flowchart of a monitoring range updating step that is performed in an actual processing step (S15 (step 15, hereinafter, S means a step)) of FIG. 3.

As shown in FIGS. 3 and 4, the tool abnormality determination method is performed in parallel with a production method of the workpiece. The tool abnormality determination method detects an abnormality in the tool bit 28 based on a change in current value of the spindle motor 42. The current value of the spindle motor 42 is included in the concept of the "load data" of the present invention.

The production method of the workpiece W has a teaching process (S1 to S10 of FIG. 3) and a processing process (S11 to S17 of FIG. 3). In each of the teaching process and the processing process, a cycle is repeated a predetermined number of times. The cycle has an air-cut step A1 (S3, S11 of FIG. 3) and an actual processing step A2 (S4, S15 of FIG. 3).

The control device 22 shown in FIG. 2 can recognize the starting point and the end point of the air-cut step A1 and the starting point and the end point of the actual processing step A2 from, e.g., a processing command (G-codes etc.) of a processing program for the workpiece W. The processing program stored in the storage section 220*a* uses G-codes such as "G0," "G1," and "G2." "G0" is a G-code for positioning of the tool bit 28, and is used to move the tool bit 28 from another position to a target position when starting processing of a desired processing part of the workpiece W. "G0" is also used to move the tool bit 28 from the target position to another position when the processing of the desired processing part of the workpiece W is finished.

"G1" is a G-code for movement of the tool bit 28 in a linear direction, and is used to move the tool bit 28 in the X-axis or Z-axis direction during processing of the workpiece W. "G2" is a G-code for movement of the tool bit 28 in an arc direction, and is used to move the tool bit 28 in the arc direction during processing of the workpiece W. Other G-codes may be used including "G3" as a G-code for movement of the tool bit 28 in an arc direction (the opposite direction from "G2").

In this example, "N" represents the total number of workpieces W to be produced (the total number of cycles) (N=50), "n" represents the number of workpieces W to be produced in the teaching process (the number of cycles to be repeated in the teaching process (n=10), and the number of workpieces W to be produced in the processing process (the number of cycles to be repeated in the processing process) is 40.

The tool abnormality determination method has a first sampling step (S3, S4 of FIG. 3), a peak hold step (S5 of FIG. 3), an early-stage data computation step (S7 of FIG. 3), a monitoring range setting step (S8 of FIG. 3), a monitoring period setting step (S9 of FIG. 3), a number-of-consecutive-times threshold setting step (S10 of FIG. 3), a second sampling step (S11 of FIG. 3), a later-stage data computation step (S12 of FIG. 3), a load ratio computation step (S13 of FIG. 3), a monitoring range correction step (S14 of FIG. 3), a monitoring range update step (S21 to S26 of FIG. 4), and a manual update step.

<Steps of Tool Abnormality Determination Method to be Performed in Teaching Process of Production Method of Workpiece W>

In the teaching process, the control device 22 in FIG. 2 sets a monitoring range to be used in the subsequent processing process. That is, in the teaching process, ten workpieces W are produced in the state where the monitoring range has not been set.

The first sampling step, the peak hold step, the early-stage data computation step, the monitoring range setting step, the monitoring period setting step, and the number-of-consecutive-times threshold setting step are performed in the teaching process. Each of these steps will be described below.

[First Sampling Step and Peak Hold Step]

Figure 5:
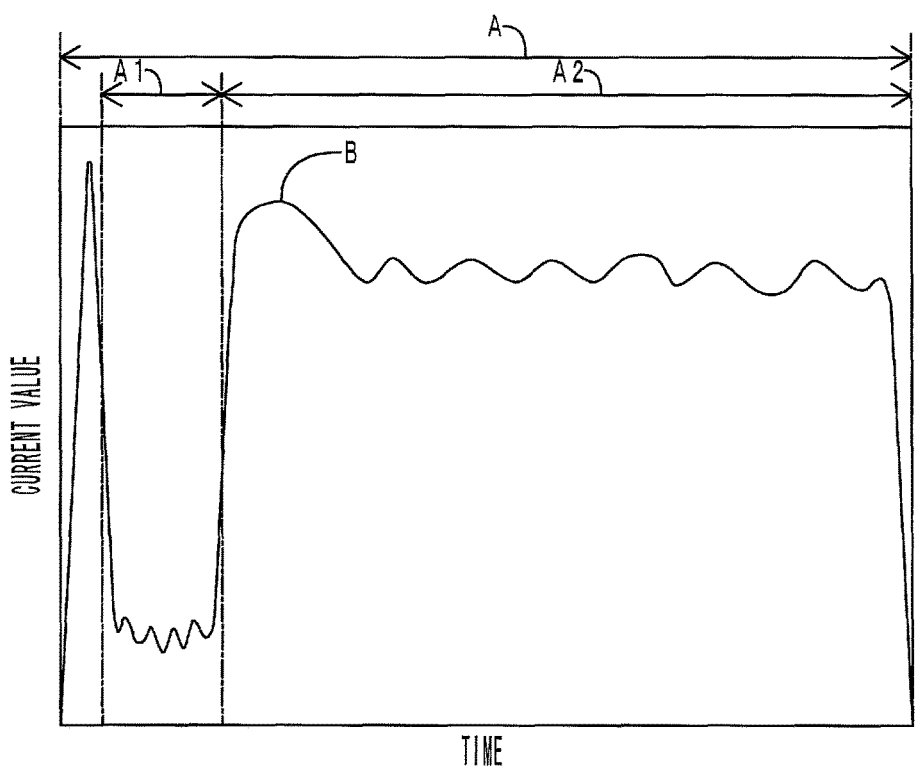
FIG. 5 is a graph showing a change in current value with time in a first sampling step (first cycle) of the tool abnormality determination method.
Figure 6:
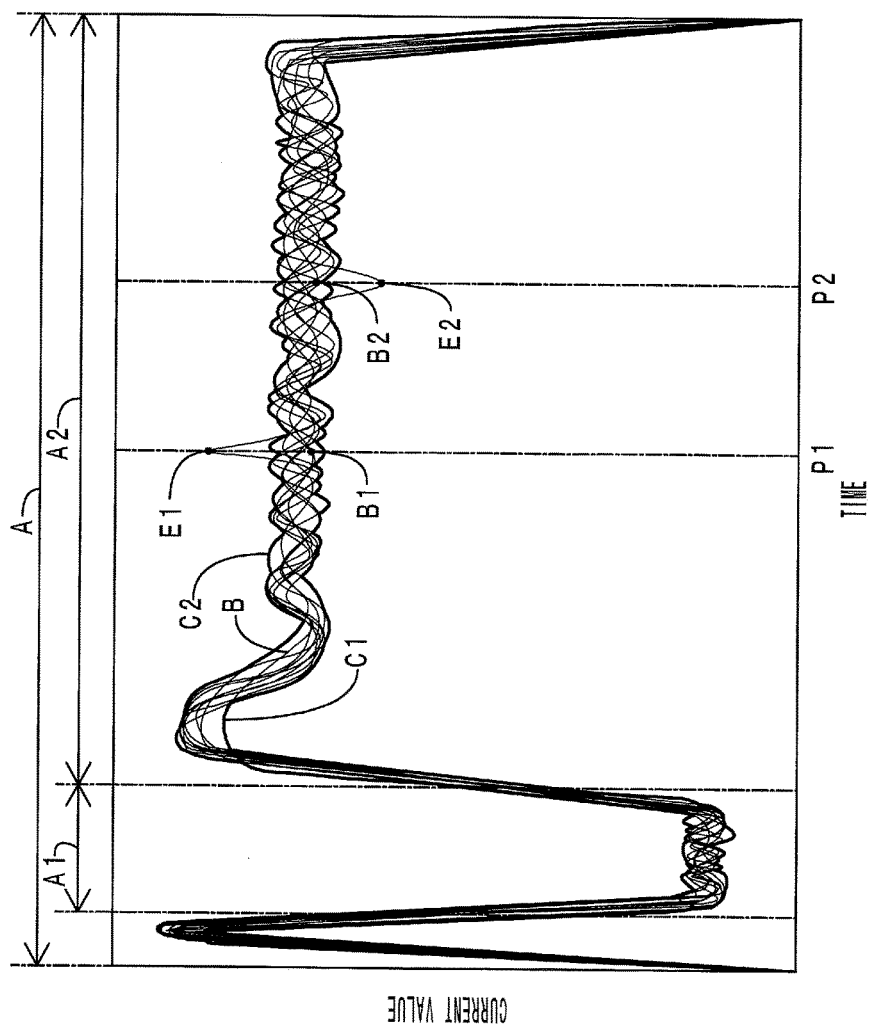
FIG. 6 is a graph showing a low load-side peak hold value and a high load-side peak hold value which are set in a peak hold step of the tool abnormality determination method.

FIG. 5 shows a change in current value with time in the first sampling step (first cycle) of the tool abnormality determination method that is performed by using the tool abnormality determination system of the present embodiment. FIG. 6 shows a low load-side peak hold value and a high load-side peak hold value that are set in the peak hold step of the tool abnormality determination method. Specifically, FIG. 6 shows a low load-side peak hold value C1 and a high load-side peak hold value C2 after the tenth first sampling step.

The control device 22 in FIG. 2 repeats the first sampling step (S3, S4 of FIG. 3) and the peak hold step (S5 of FIG. 3) ten times in this order. That is, a current value is detected for ten workpieces W.

Specifically, the operator first inputs the number of teachings (10 times) and an offset amount (5%) to the control device 22 via the screen 23 shown in FIG. 2 (S1, S2 of FIG. 3). Next, the control device 22 drives the spindle motor 42 to rotate the chuck 3, i.e., a workpiece W, about its own axis. Then, the control device 22 drives the X-axis motor 72 and the Z-axis motor 63 to move the tool bit 28 to a predetermined processing part of the workpiece W (S3 of FIG. 3). Thereafter, the control device 22 moves the tool bit 28 as appropriate in the left-right and up-down directions to cut the predetermined processing part of the workpiece W (S4 of FIG. 3).

In the first sampling step (S3, S4 of FIG. 3), the control device 22 detects a current value of the spindle motor 42 at predetermined intervals (e.g., every 30 ms). If the current number of cycles A is 10 or less (S6 of FIG. 3), the control device 22 repeats the first sampling step (S3, S4 of FIG. 3) and the peak hold step (S5 of FIG. 3). That is, the peak hold step is performed every time the cycle A is completed. The control device 22 in FIG. 2 stores in the storage section 220a a current value of the first cycle A shown in FIG. 5 as reference data B.

For example, when the second cycle A is completed, the control device 22 compares the current value of the first cycle A with that of the second cycle A for each processing point. Since each cycle A has the same processing route, the time on the abscissa in FIGS. 5 and 6 corresponds to the processing points of the workpiece W. The control device 22 superimposes the current values of two cycles so that the processing points in one of the cycles correspond to those in the other cycle. For each processing point, the smaller one of the current values of the two cycles is set as a low load-side peak hold value, and the larger one of the current values of the two cycles is set as a high load-side peak hold value.

As shown in FIG. 6, a band-shaped pattern is obtained by superimposing the current values for ten cycles. In the tenth peak hold step (S5 of FIG. 3), the control device 10 in FIG. 2 obtains the low load-side peak hold value C1 and the high load-side peak hold value C2 for the ten cycles as continuous curves, as shown by thick lines in FIG. 6.

The control device 22 in FIG. 2 stores in the storage section 220a the current values for the ten cycles, the low load-side peak hold value C1, and the high load-side peak hold value C2 shown in FIG. 6.

Some of the current values for the ten cycles significantly deviate from the reference data B shown in FIG. 5. For example, for a processing point P1 shown in FIG. 6, a current value E1 significantly deviates upward from reference data B1. Similarly, for a processing point P2, a current value E2 significantly deviates downward from reference data B2.

A teaching lower limit threshold F1 is calculated by the following formula.

$$F1 = t - (t \times h) \tag{1}$$

where "h" represents a teaching offset amount (10%), and "t" represents a current value of the reference data B1, B2 at any processing point P1, P2.

Similarly, a teaching upper limit threshold F2 is calculated by the following formula.

$$F2 = t + (t \times h) \tag{2}$$

Since the current value E1 is larger than the teaching upper limit threshold F2, the current value E1 is excluded when obtaining the high load-side peak hold value C2. Since the current value E2 is lower than the teaching lower limit threshold F1, the current value E2 is automatically excluded when obtaining the low load-side peak hold value C1.

A part of the current values which is lower than the teaching lower limit threshold F1 and is larger than the teaching upper limit threshold F2 is excluded when obtaining the low load-side peak hold value C1 and the high load-side peak hold value C2. The control device 22 shown in FIG. 2 stores the teaching offset amount "h," the teaching lower limit threshold F1, and the teaching upper limit threshold F2 in the storage section 220a.

[Early-Stage Data Computation Step]

In this step, the control device 22 in FIG. 2 calculates early-stage data from all the current values detected in the air-cut steps A1 shown in S3 of FIG. 3 (e.g., m (points per cycle)×10 (cycles) current values in the case where the current values are detected at m points in the air-cut step A1 of each cycle A). Specifically, the control device 22 calculates an average value of all the current values as early-stage data L1, and stores the early-stage data L1 in the storage section 220a.

[Monitoring Range Setting Step]

Figure 7:
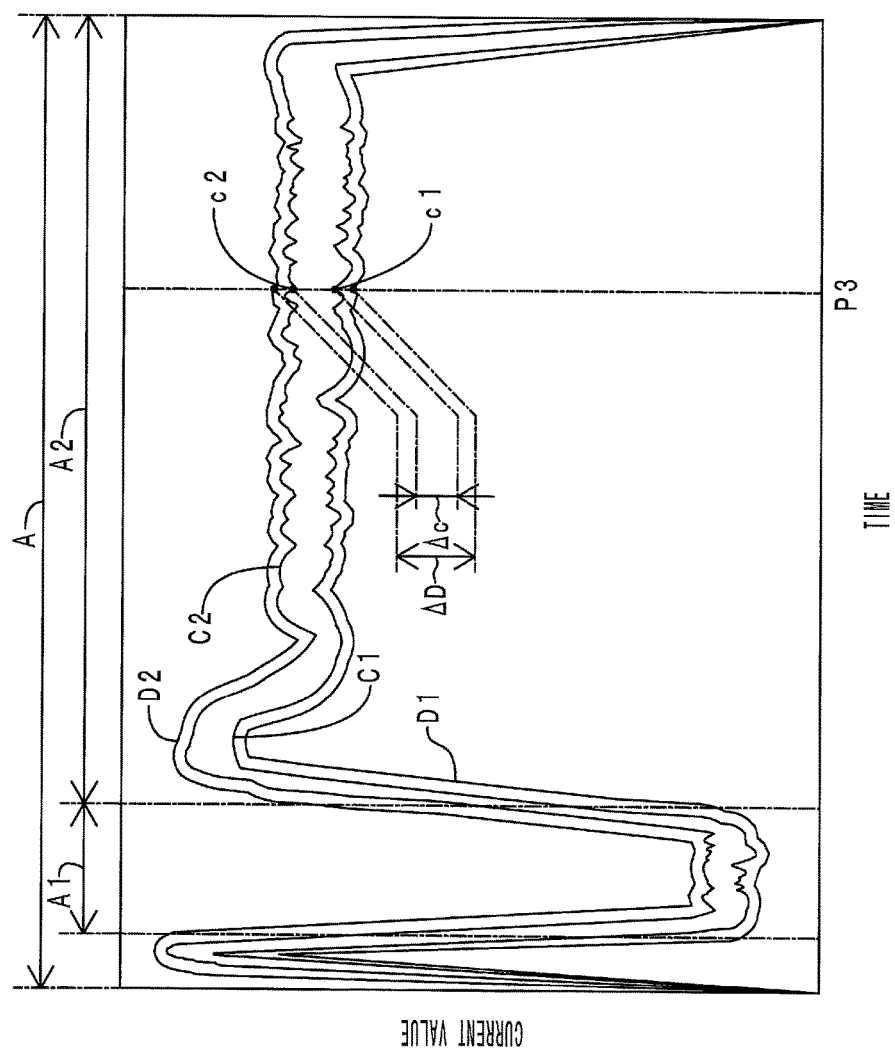
FIG. 7 is a graph showing a monitoring range that is set in a monitoring range setting step of the tool abnormality determination method.

FIG. 7 shows a monitoring range that is set in the monitoring range setting step of the tool abnormality determination method that is performed by using the tool abnormality determination system of the present embodiment. In this step, the control device 22 sets a monitoring range $\Delta D$ based on the low load-side peak hold value C1 and the high load-side peak hold value C2 (S8 of FIG. 3). Specifically, the control device 22 corrects the low load-side peak hold value C1 and the high load-side peak hold value C2 by using the offset amount (5%) set in S2 of FIG. 3, thereby calculating a lower limit threshold D1 and an upper limit threshold D2.

The lower limit threshold D1 is calculated by the following formula.

$$D1 = c1 - (\Delta c \times H) \tag{3}$$

where "H" represents the offset amount (5%), and "$\Delta c$" represents the difference between the low load-side peak hold value c1 and the high load-side peak hold value c2 at any processing point P3.

Similarly, the upper limit threshold D2 is calculated by the following formula.

$$D2 = c2 + (\Delta c \times H) \tag{4}$$

The monitoring range $\Delta D$ is calculated by the following formula.

$$\Delta D = D2 - D1 \tag{5}$$

In this step, the control device 22 in FIG. 2 thus sets the monitoring range $\Delta D$ based on the low load-side peak hold value C1 and the high load-side peak hold value C2. The control device 22 stores the offset amount H and the monitoring range $\Delta D$ (the lower limit threshold D1, the upper limit threshold D2) in the storage section 220a.

[Monitoring Period Setting Step]

Figure 8:
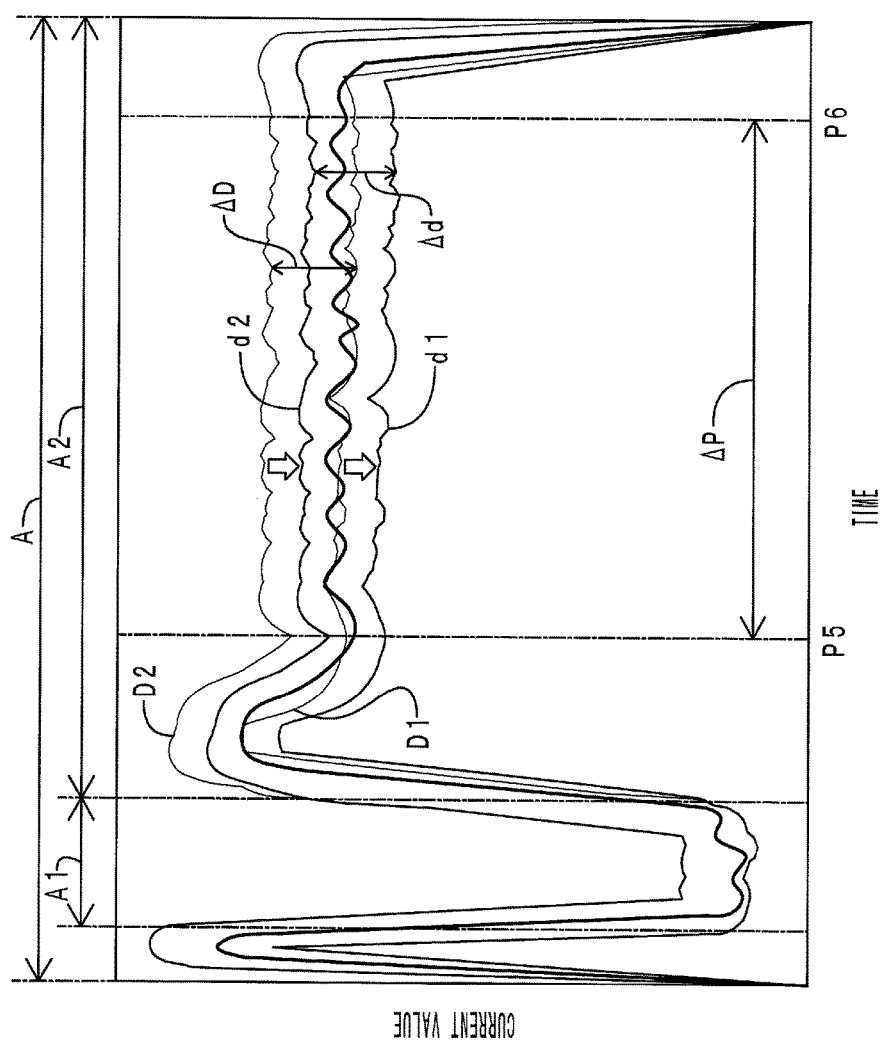
FIG. 8 is a graph showing a change in current value with time in a second sampling step of the tool abnormality determination method.

FIG. 8 shows a change in current value with time in the second sampling step of the tool abnormality determination method that is performed by using the tool abnormality determination system of the present embodiment. In this step, as shown in FIG. 8, the period between a starting point (time) P5 and an end point (time) P6 is set as a monitoring period $\Delta P$ (S9 of FIG. 3).

The monitoring period $\Delta P$ is set as follows. The control device 22 calculates the difference $\Delta G$ between the largest value GH and the smallest value GL of consecutive ten of a plurality of current values detected in the actual processing step A2 of the first cycle A of the first sampling step shown in S4 of FIG. 3.

The current of the spindle motor 42 (specifically, the current of the spindle motor 42 minus a current required for acceleration and deceleration) is normalized to (−7282 to 7282). The maximum current value (20 A) of an amplifier (not shown) of the motor drive circuit 222 corresponds to "7282."

The control device 22 sets a period during which the difference $\Delta G$ (A)$\leq$(100/7282)$\times$20 (A) (specifically, a period during which this inequality is satisfied) as the monitoring period $\Delta P$. The rate of change of the current (i.e., load) (current/time) is low in this monitoring period $\Delta P$. The current is therefore stable in the monitoring period $\Delta P$. The control device 22 stores the monitoring period $\Delta P$ in the storage section 220*a*.

[Number-of-Consecutive-Times Threshold Setting Step]

In this step, the operator inputs a number-of-consecutive times threshold "k" (a threshold for the number of consecutive times the current value is out of the monitoring range $\Delta D$ in S15 of FIG. 3) to the control device 22 via the screen 23 (S10 of FIG. 3). The control device 22 stores the number-of-consecutive times threshold "k" (2 in the present embodiment) in the storage section 220*a*.

<Steps of Tool Abnormality Determination Method to be Performed in Processing Process of Production Method of Workpiece W>

In the processing process, the control device 22 in FIG. 2 performs processing of the workpiece W while monitoring the load on the tool bit 28 (specifically, the current value of the spindle motor 42) by using the monitoring range $\Delta D$ (specifically, a monitoring range $\Delta d$ as a corrected monitoring range $\Delta D$). That is, in the processing process, forty workpieces W are produced in the state where the monitoring range $\Delta D$ has been set.

The second sampling step, the later-stage data computation step, the load ratio computation step, the monitoring range correction step, the monitoring range update step, and the manual update step are performed in the processing process. Each of these steps will be described below.

[Second Sampling Step, Later-Stage Data Computation Step, and Load Ratio Computation Step]

As shown in S11 of FIG. 3, the second sampling step is performed in the air-cut steps A1 of the forty cycles A in the processing process. Specifically, the control device 22 detects the current value of the spindle motor 42 at predetermined intervals. That is, the control device 22 detects the current value every time the air-cut step A1 is performed in any of the cycles A.

In the later-stage data computation step shown in S12 of FIG. 3, the control device 22 in FIG. 2 calculates later-stage data from a plurality of current values detected in the air-cut step A1 shown in S11 of FIG. 3 (a plurality of current values detected in the air-cut step A1 of a single cycle A). Specifically, the control device 22 calculates an average value of all the current values as later-stage data L2, and stores the later-stage data L2 in the storage section 220*a*.

In the load ratio computation step shown in S13 of FIG. 3, the control device 22 computes the load ratio R from the early-stage data L1 and the later-stage data L2 by using the following formula.

$$R = L2/L1 \quad (6)$$

For example, in the case where the early-stage data L1 is detected before idling of the lathe 1 and the later-stage data L2 is detected after idling of the lathe 1, L1>L2, i.e., R<1 because mechanical efficiency of each part of the lathe 1 is higher after idling than before idling.

On the other hand, in the case where the early-stage data L1 is detected after idling of the lathe 1 and the later-stage data L2 is detected before idling of the lathe 1 (e.g., the morning after the day the early-stage data L1 was detected), L1<L2, i.e., R>1. The detected load ratio R thus varies according to the state of the lathe 1.

[Monitoring Range Correction Step]

The second sampling step is performed in parallel with the air-cut step A1 of FIG. 8. In the case where the first sampling step shown in S3 of FIG. 3 is performed before idling of the lathe 1 and the second sampling step shown in S11 of FIG. 3 is performed after idling of the lathe 1, the monitoring range $\Delta D$ reflects low mechanical efficiency before idling because the monitoring range $\Delta D$ has been set based on the current values detected before idling. Idling has been completed when the second sampling step is performed. Accordingly, the current value decreases according to high mechanical efficiency. The current value therefore tends to be lower than the lower limit threshold D1 of the monitoring range $\Delta D$, as shown in the air-cut step A1 of FIG. 8.

On the other hand, in the case where the first sampling step shown in S3 of FIG. 3 is performed after idling of the lathe 1 and the second sampling step shown in S11 of FIG. 3 is performed before idling of the lathe 1 (e.g., the morning after the day the early-stage data L1 was detected), the current value tends to be larger than the upper limit threshold D2 of the monitoring range $\Delta D$. If the state of the lathe 1 during detection of the current value is thus different from that of the lathe 1 during setting of the monitoring range $\Delta D$, the current value tends to be out of the monitoring range $\Delta D$ even though the tool bit 28 is in a normal state.

In this step, the control device 22 therefore corrects the monitoring range $\Delta D$ (i.e., the lower limit threshold D1, the upper limit threshold D2) by using the load ratio R calculated by Formula (6). The corrected lower and upper limit thresholds d1, d2 are calculated by the following formulas.

$$d1 = D1 \times R \quad (7)$$

$$d2 = D2 \times R \quad (8)$$

The corrected monitoring range $\Delta d$ is therefore calculated by the following formula.

$$\Delta d = d2 - d1 \quad (9)$$

In this step, the monitoring range $\Delta D$ is thus corrected to the monitoring range $\Delta d$. As shown in FIG. 8, the corrected monitoring range $\Delta d$ is used in the actual processing step A2 immediately after the second sampling step (i.e., the air-cut step A1). For example, in the case where the early-stage data L1 is detected before idling of the lathe 1 and the later-stage data L2 is detected after idling of the lathe 1, L1>L2, i.e., R<1 because the mechanical efficiency of each part of the lathe 1 is higher after idling than before idling. Accordingly, the lower limit threshold d1 is shifted downward with respect to the lower limit threshold D1, and the upper limit threshold d2 is shifted downward with respect to the upper limit threshold D2, as shown by white arrows in FIG. 8.

[Monitoring Range Update Step]

Figure 9:
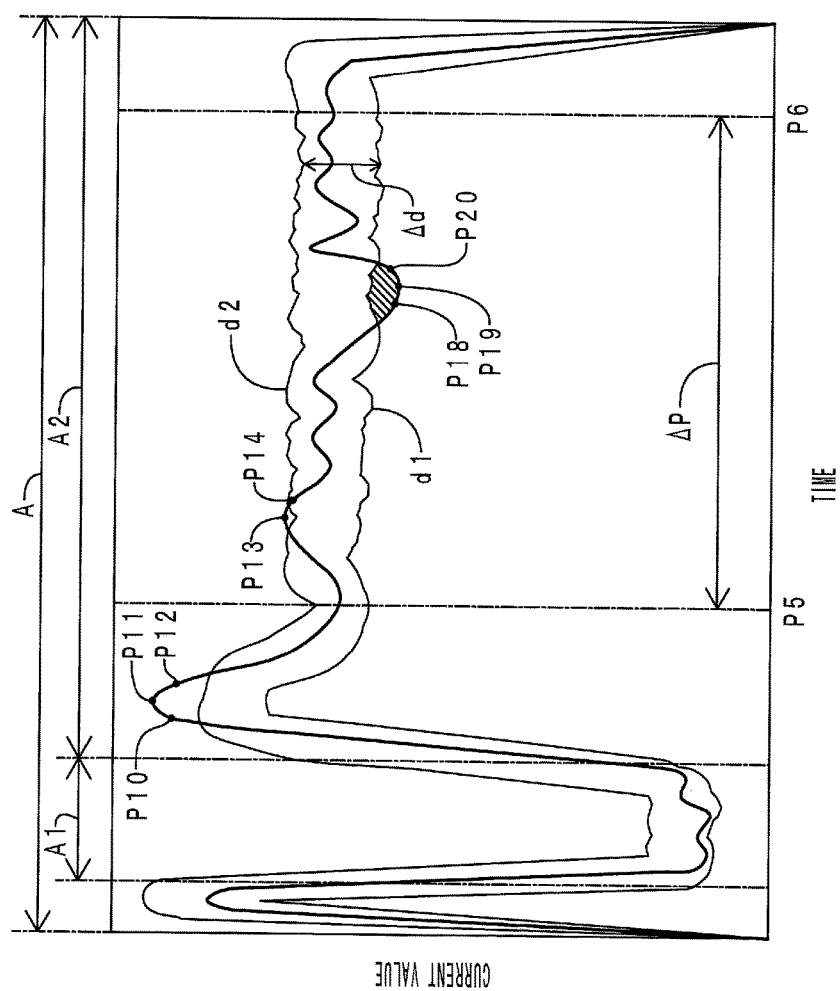
FIG. 9 is a graph showing a change in current value with time in the monitoring range update step of the tool abnormality determination method.

FIG. 9 shows a change in current value with time in the monitoring range update step of the tool abnormality determination method that is performed by using the tool abnormality determination system of the present embodiment. This step is performed in parallel with the actual processing step A2 (S15 of FIG. 3) in the processing process. That is, in this step, the workpiece W is processed while monitoring the tool bit 28 for abnormalities by using the corrected monitoring range $\Delta d$.

Specifically, the he control device 22 in FIG. 2 drives the spindle motor 42 to rotate the chuck 3, i.e., the workpiece W, about its own axis. Then, the control device 22 drives the X-axis motor 72 and the Z-axis motor 63 to move the tool bit 28 as appropriate in the left-right and up-down directions, thereby cutting the workpiece W (S21 of FIG. 4).

The control device 22 determines if the current value detected at predetermined intervals is included in the monitoring period ΔP shown in FIG. 9 (S22 of FIG. 4). For example, in the early stage of the actual processing step A2, the current value of the spindle motor 42 can increase rapidly as the step proceeds from the air-cut step A1, like current values P10 to P12 shown in FIG. 9. The current value therefore is out of the monitoring range Δd. However, the current values P10 to P12 have been detected before the starting point P5 of the monitoring period ΔP. That is, none of the current values P10 to P12 is included in the monitoring period ΔP. Accordingly, the control device 22 does not compare the current values P10 to P12 with the monitoring range Δd. That is, the control device 22 does not monitor the current values P10 to P12.

The current values that are detected after the starting point P5 are included in the monitoring period ΔP (S22 of FIG. 4). The control device 22 therefore starts monitoring the current value (S23 of FIG. 4). That is, the control device 22 compares the current value with the monitoring range Δd.

If the current value is within the monitoring range Δd, the actual processing step A2 for the workpiece W is completed (S24 of FIG. 4). If there is any subsequent workpiece W to be processed, that is, if the number of cycles that have been performed is less than 50 in the processing process of FIG. 3, the routine proceeds to the air-cut step A1 for the subsequent workpiece W (S16, S11 of FIG. 3). If there is no subsequent workpiece W to be processed, that is, the number of cycles that have been performed is 50 in the processing process of FIG. 3, production of the workpieces W is completed (S17 of FIG. 3).

On the other hand, if the current value is out of the monitoring range Δd, the control device 22 counts the number of consecutive times the current value is out of the monitoring range Δd (S25 of FIG. 4). If the number of consecutive times does not exceed the number-of-consecutive-times threshold (2 times), the control device 22 continues to monitor the current value (S23 of FIG. 4).

For example, a current value P13 shown in FIG. 9 is out of the monitoring range Δd, but the subsequent current value P14 is within the monitoring range Δd. The number of consecutive times the current value is out of the monitoring range Δd is therefore 1. In this case, the control device 22 continues to monitor the current value (S23 of FIG. 4).

If the number of consecutive times exceeds the number-of-consecutive-times threshold (2 times) (S25 of FIG. 4), the control device 22 stops the lathe 1 as soon as the current value is out of the monitoring range Δd, and displays guidance on the screen 23 (S26 of FIG. 4).

For example, current values P18 to P20 shown in FIG. 9 is out of the monitoring range Δd. That is, the number of consecutive times the current value is out of the monitoring range Δd is three (>2 times) (S25 of FIG. 4). In this case, the control device 22 stops the lathe 1 and displays guidance on the screen 23 (S26 of FIG. 4).

As shown in FIG. 4, current values similar to those of FIG. 9 are displayed on the screen 23. A question 233 "Any chipping?" is displayed on the screen 23. A "Yes" button 230, a "No" button 231, and a "Cancel" button 232 are also displayed for the operator to input an answer to the question 233.

The operator visually checks the tool bit 28 shown in FIG. 1. If the operator sees any chipping of the blade of the tool bit 28, that is, if the tool bit 28 is in a main abnormal state, he/she presses the "Yes" button 230 on the screen 23. If the operator does not see any chipping of the blade of the tool bit 28, and the tool bit 28 is in a normal state (e.g., the tool bit 28 has merely been worn), he/she presses the "No" button 231 on the screen 23. If the operator does not see any chipping of the blade of the tool bit 28, but the tool bit 28 is in any other abnormal state (e.g., chips of the workpiece W have been stuck in the tool bit 28, the tool bit 28 has not been mounted on the tool rest 20, the X-axis motor 72, the Z-axis motor 63, or the spindle motor 42 of FIG. 2 has not been operating properly, the cutting program stored in the storage section 220a of FIG. 2 has not been operating properly, etc.), that is, if the tool bit 28 is in a sub abnormal state, he/she presses the "Cancel" button 232 on the screen 23.

If the "Yes" button 230 or the "Cancel" button 232 is pressed by the operator, the actual processing step A2 for the workpiece W is completed (S24 of FIG. 4). If there is any subsequent workpiece W to be processed, the routine proceeds to the air-cut step S1 for the subsequent workpiece W (S16, S11 of FIG. 3). If there is no subsequent workpiece W to be processed, production of the workpieces W is completed (S17 of FIG. 3). In this case, the control device 22 does not update the monitoring range Δd.

If the "No" button 231 is pressed by the operator, the control device 22 updates the monitoring range Δd. That is, if the "No" button 231 is pressed by the operator, this means that the current value shown in FIG. 9 is lower than the lower limit threshold d1 even though the tool bit 28 is in a normal state. In this case, the control device 22 in FIG. 2 performs the peak hold by using a part (hatched part in FIG. 9) of the current values of FIG. 9 which is lower than the lower limit threshold d1. Specifically, the control device 22 corrects the low load-side peak hold value C1 shown in FIG. 7, and recalculates the lower limit threshold D1, the upper limit threshold D2, and the monitoring range ΔD by using Formulas (3) to (5).

The current values shown in FIG. 9 are reflected in the updated monitoring range ΔD. The control device 22 in FIG. 2 stores the new monitoring range ΔD (the lower limit threshold D1, the upper limit threshold D2) in the storage section 220a. As processing of the workpiece W progresses to the end point P6 of the monitoring period ΔP or later, the control device 22 finishes monitoring of the current value (S22 of FIG. 4).

If there is any subsequent workpiece W to be processed, the control device 22 uses the updated monitoring range ΔD from the subsequent workpiece W. That is, the control device 22 corrects the updated monitoring range ΔD by Formulas (7) to (9) to calculate the monitoring range Δd. As shown in FIG. 8, the control device 22 thus uses the monitoring range Δd to monitor the tool bit 28 for abnormalities in the actual processing step A2 for the subsequent workpiece W.

[Manual Update Step]

In this step, the operator manually updates the monitoring range ΔD. That is, the operator adjusts the lower limit threshold D1 and the upper limit threshold D2 for every processing point of the workpiece W. This adjustment work is carried out by switching the screen 23 to a number input mode by the control device 22 in FIG. 2 and inputting the lower limit threshold D1 and the upper limit threshold D2 on the screen by the operator. The control device 22 displays the monitoring range ΔD reflecting the manually input lower and upper limit thresholds D1, D2 on the screen 23.

(Advantageous Effects)

Advantageous effects of the tool abnormality determination system 2 of the present embodiment will be described. According to the tool abnormality determination system 2 of the present embodiment, the monitoring range ΔD in the actual processing step A2 (specifically, the monitoring period ΔP) of the cycle A of the processing process can be corrected by using the current value of the spindle motor 42 in the air-cut step A1 of the cycle A of the teaching process and the current value of the spindle motor 42 in the air-cut step A1 of the cycle A of the processing process. This allows an abnormality of the tool bit 28 to be accurately detected regardless of when the monitoring range ΔD is set in S8 of FIG. 3 (e.g., before idling, after idling, etc.).

The workpiece W shown in FIG. 1 is processed in the actual processing step A2 of the cycle A. Variation in shape, material etc. among the workpieces W therefore tends to be reflected in the current value of the spindle motor 42. According to the tool abnormality determination system 2 of the present embodiment, since both the current value for the early-stage data L1 and the current value for the later-stage data L2 are detected in the air-cut step A1 of moving the tool bit 28, variation among the workpieces W is less likely to be reflected in the load ratio R.

According to the tool abnormality determination system 2 of the present embodiment, the monitoring range ΔD can be corrected for the entire monitoring period ΔP by using the load ratio R shown by Formulas (7) to (9), as shown in FIG. 8.

According to the tool abnormality determination system 2 of the present embodiment, as shown in S3 of FIG. 3, the current value for the early-stage data L1 is detected in the air-cut step A1 of the cycle A of the teaching process. That is, since the current value that is detected in the air-cut step A1 of the cycle A of the teaching process is used to set the monitoring range ΔD and to correct the monitoring range ΔD, the state of the load during setting of the monitoring range ΔD can be reflected in the load ratio R.

According to the tool abnormality determination system 2 of the present embodiment, the monitoring range ΔD can be changed at least for the entire monitoring period ΔP by the monitoring range correction step (S14 of FIG. 3), as shown in FIG. 8. That is, the overall monitoring range ΔD can be changed.

According to the tool abnormality determination system 2 of the present embodiment, the monitoring range ΔD can be changed processing point by processing point by the monitoring range update step (S21 to S26 of FIG. 4) and the manual update step, as shown in FIG. 9. That is, the monitoring range ΔD can be changed locally. Thus combining "correction" and "update" of the monitoring range ΔD can automatically and continuously improve the monitoring range ΔD without increasing a work load on the operator.

In the case where the monitoring range correction step (S14 of FIG. 3) is not performed, the current value after idling (high mechanical efficiency) that is later in time tends to be lower than the monitoring range ΔD set before idling (low mechanical efficiency), as shown in FIG. 8. Therefore, the monitoring range update step (S21 to S26 of FIG. 4) is performed frequently. In this case, the operator needs to frequently visually check the tool bit 28 of FIG. 1 and press the "Yes" button 230 on the screen 23 shown in S26 of FIG. 4, which is troublesome. Moreover, the lower limit threshold D1 of the monitoring range ΔD is gradually shifted downward by this operation, which increases the monitoring range ΔD.

On the contrary, for the monitoring range ΔD set after idling, the current value before idling that is later in time tends to be larger than the monitoring range ΔD. In this case, the upper limit threshold D2 of the monitoring range ΔD is gradually shifted upward, which increases the monitoring range ΔD.

The tool abnormality determination system 2 of the present embodiment is capable of performing the monitoring range correction step (S14 of FIG. 3). The operator therefore does not need to frequently update the monitoring range ΔD. The monitoring range ΔD is less likely to be increased by the difference between before and after idling (change in mechanical efficiency).

The tool abnormality determination system 2 of the present embodiment prompts the operator with the question 233 "Any chipping?" as shown in S26 of FIG. 4, when the load on the tool bit 28 is out of the monitoring range ΔD. The operator can check if the tool bit 28 is actually in an abnormal state or not by either directly checking the tool bit 28 or indirectly checking the tool bit 28 by using a current value graph on the screen 23 etc. That is, the operator can recognize if the monitoring range ΔD is appropriate or not. This can easily improve accuracy of the monitoring range ΔD.

According to the tool abnormality determination system 2 of the present embodiment, high accuracy of the monitoring range ΔD can ensure a stable cutting surface for the tool bit 28. Moreover, the high accuracy of the monitoring range ΔD allows the tool bit 28 to be used until just before chipping occurs.

In the first sampling process of the tool abnormality determination method, the control device 22 detects the current values for a total of 10 cycles A while performing the peak hold in each cycle A (S3, S4 of FIG. 3). As shown in FIG. 6, the control device 22 can therefore set the smallest one of the current values for the 10 cycles as the low load-side peak hold value C1, and can set the largest one of the current values for the 10 cycles as the high load-side peak hold value C2.

According to the tool abnormality determination system 2 of the present embodiment, the control device 22 thus sets the low load-side peak hold value C1 and the high load-side peak hold value C2 by superimposing the actually detected current values. The control device 22 also sets the monitoring range ΔD based on the low load-side peak hold value C1 and the high load-side peak hold value C2, as shown by Formulas (3) to (5). This eliminates the need for a complicated computation process and facilitates visual checking.

In the first sampling step, the peak hold step, and the monitoring range setting step, no question about whether the tool bit 28 is in an abnormal state or not is displayed on the screen 23 shown in FIG. 4. This allows the first sampling step, the peak hold step, and the monitoring range setting step to be smoothly performed.

In the peak hold step, as shown in FIG. 6 and Formulas (1) and (2), a part of the current values which is lower than the teaching lower limit threshold F1 and is larger than the teaching upper limit threshold F2 is excluded when obtaining the low load-side peak hold value C1 and the high load-side peak hold value C2. Abnormal current values are therefore less likely to be reflected in the monitoring range ΔD. This can improve accuracy of the monitoring range ΔD.

In the monitoring range setting step shown in S8 of FIG. 3, the control device 22 sets the monitoring range ΔD by using Formulas (3) to (5). As shown in FIG. 7, the lower limit threshold D1 and the upper limit threshold D2 change according to the difference Δc between the low load-side peak hold value c1 and the high load-side peak hold value c2.

That is, at a processing point with a large difference Δc, namely at such a processing point that the current values for the 10 cycles in the sampling step vary significantly, the lower limit threshold D1 is significantly lower than the low load-side peak hold value c1, and the upper limit threshold D2 is significantly larger than the high load-side peak hold value c2, which increases the monitoring range ΔD.

On the other hand, at a processing point with a small difference Δc, namely at such a processing point that the current values for the 10 cycles in the sampling step vary only slightly, the lower limit threshold D1 is slightly lower than the low load-side peak hold value c1, and the upper limit threshold D2 is slightly larger than the high load-side peak hold value c2, which reduces the monitoring range ΔD. According to the tool abnormality determination system 2 of the present embodiment, the gap between the lower limit threshold D1 and the upper limit threshold D2 (the monitoring range ΔD) can be changed according to the processing point of the workpiece W.

In the processing process of FIG. 3, the eleventh and subsequent cycles A are performed. That is, the workpiece W is actually cut by using the set monitoring range ΔD. As shown in S26 of FIG. 4, if the current value of the tool bit 28 is out of the monitoring range Δd three consecutive times, the screen 23 prompts the operator with the question 233 "Any chipping?" In response to the question, the operator checks the state of the tool bit 28.

If the operator actually sees chipping of the tool bit 28, he/she presses the "Yes" button 230. This means that the control device 22 was able to determine that the tool bit 28 had been chipped. Since the determination of the control device 22 is appropriate, the control device 22 does not update the monitoring range ΔD. On the other hand, if the operator checks the tool bit 28 and finds that the tool bit 28 is actually in a normal state (e.g., the tool bit 28 has merely been worn), he/she presses the "No" button 231. This means that the control device 22 failed to determine that the tool bit 28 was in a normal state. Since the determination of the control device 22 is inappropriate, the control device 22 updates the monitoring range ΔD (monitoring range update step).

If the operator checks the tool bit 28 and finds that there is no chipping of the blade of the tool bit 28, but the tool bit 28 is in other abnormal state, he/she presses the "Cancel" button 232. This means that the control device 22 erroneously determined that the tool bit 28 had been chipped and failed to determine that the tool bit 28 was in other abnormal state. In this case, the control device 22 does not update the monitoring range ΔD although the determination of the control device 22 is inappropriate. This is because this abnormal state is reflected in the monitoring range ΔD if the monitoring range ΔD is updated in this case. According to the tool abnormality determination system 2 of the present embodiment, the monitoring range can be updated only when the control device 22 failed to determine that the tool bit 28 was in a normal state. This can improve accuracy of the monitoring range.

It is herein assumed that the lathe 1 stopped due to chips of the workpiece W being stuck in the tool bit 28, but the chips had already fallen off when the operator checked the tool bit 28. In this case, no chipping has occurred in the tool bit 28. Accordingly, the operator cannot directly see the abnormal state. However, as shown in S26 of FIG. 4, how the current value changed with time (history) just before the lathe 1 stopped is shown next to the "Yes" button 230, the "No" button 231, and the "Cancel" button 232 on the screen 23. This allows the operator to infer from the current value and the state of the tool bit 28 that the chips of the workpiece W had been stuck in the tool bit 28 when the lathe 1 stopped. According to the tool abnormality determination system 2 of the present embodiment, an abnormal state can be inferred from the graph of the current value on the screen 23.

In the manual update step, the operator can manually update the monitoring range ΔD. Accordingly, the operator can manually decrease the upper limit threshold D2 when he/she has visually checked chipping and the current value is within the monitoring range ΔD, etc. Similarly, the operator can manually increase the lower limit threshold D1. According to the tool abnormality determination system 2 of the present embodiment, the monitoring range ΔD that tends to be widened by the peak hold step can be narrowed manually.

The "Yes" button 230 and the "Cancel" button 232 are displayed on the screen 23. The "Yes" button 230 corresponds to chipping of the tool bit 28 (main abnormal state), and the "Cancel" button 232 corresponds to an abnormal state (sub abnormal state) other than the chipping. The control device 22 stores which button was pressed in the storage section 220a. This facilitates collection of data on the abnormal states and classification of factors for the abnormal states.

As shown in S22 of FIG. 4, if the current value is out of the monitoring period ΔP, the control device 22 does not monitor the current value even if the current value is out of the monitoring range ΔD. Thus, a period during which the influence of a disturbance factor tends to be reflected in the current value, such as when the actual processing step is started, can be intentionally excluded from the monitoring period ΔP. This can suppress occurrence of erroneous determination, and thus can reduce complex work to be performed by the operator.

As shown in S25 of FIG. 4, the control device 22 stops the lathe 1 only when the number of consecutive times the current value is out of the monitoring range exceeds the number-of-consecutive-times threshold. As shown in S26 of FIG. 4, the control device 22 displays guidance on the screen 23. This can reduce occurrence of erroneous determination in the case where the current value is out of the monitoring range Δd by the influence of an unexpected disturbance factor, such as foreign matter adhering to the workpiece W, and thus can reduce complex work to be performed by the operator.

(Other)

The embodiment of the tool abnormality determination method of the present invention is described above. However, the present invention is not limited to the above embodiment. Various modifications and improvements can be made by those skilled in the art.

For example, the method of setting the load ratio R shown by Formula (6) is not particularly limited. The average value of all the current values detected in the actual processing steps A2 shown in S4 of FIG. 3 may be used as the early-stage data L1, and the average value of all the current values detected in the actual processing steps A2 shown in S15 of FIG. 3 may be used as the later-stage data L2.

In this case, the load ratio R for the monitoring range Δd of the second cycle A of the processing process is calculated based on the current value of the actual processing step A2 of the first (i.e., eleventh in total) cycle A of the processing process. Similarly, the load ratio R for the monitoring range Δd of the third cycle A of the processing process is calculated based on the current value of the actual processing step A2 of the second cycle A of the processing process.

This allows the load ratio R to be calculated without using the air-cut step A1. Accordingly, the monitoring range ΔD can be corrected even if, e.g., the period of the air-cut step A1 is short etc. Moreover, this time's ($M^{th}$) monitoring range ΔD can be corrected by using the current value of the previous (($M-1)^{th}$) cycle A.

The average value of all the current values detected in the actual processing steps A2 of the plurality of cycles A of the processing process may be used as the later-stage data L2. For example, if the average value of the current values for ten cycles A is used as the later-stage data L2, the load ratio R for the monitoring range Δd of the eleventh cycle A of the processing process is calculated based on the current values of the actual processing steps A2 of the first (i.e., eleventh in total) to tenth (i.e., twentieth in total) cycles A of the processing process. Similarly, the load ratio R for the monitoring range Δd of the twelfth cycle A of the processing process is calculated based on the current values of the actual processing steps A2 of the second to eleventh cycles A of the processing process.

This allows the load ratio R to be calculated without using the air-cut step A1. Accordingly, the monitoring range ΔD can be corrected even if, e.g., the period of the air-cut step A1 is short etc. Moreover, this time's ($M^{th}$) monitoring range ΔD can be corrected by using the current values of the plurality of cycles A up to the previous (($M-1)^{th}$) cycle A. Since the average value of the current values of the plurality of cycles A is used as the later-stage data L2, the influence of variation in current value by a detection error on the later-stage data L2 can be reduced.

The type of load data that is detected to set, correct, and update the monitoring range ΔD is not particularly limited. The load data need only be associated with at least one of the load of the actuator that moves the tool bit 28 (e.g., the X-axis motor 72 or the Z-axis motor 63 in FIG. 2) and the load of the actuator that moves the workpiece W (e.g., the spindle motor 42 in FIG. 2). For example, the load data may be torque, current, voltage, etc. The load data may be the total torque or total current of all the actuators, or may be the total torque or total load current of two of the actuators.

In the above embodiment, the monitoring range ΔD is corrected by using the load ratio R, as shown by Formulas (7) to (9), However, the monitoring range ΔD may be corrected by using the difference ΔL between the early-stage data L1 and the later-stage data L2. For example, the lower limit threshold d1 and the upper limit threshold d2 may be calculated by using the following formulas.

$$d1 = D1 + \Delta L \quad (10)$$

$$d2 = D2 + \Delta L \quad (11)$$

The early-stage data L1 and the later-stage data L2 may be calculated based on one or more current values in a single cycle A. The early-stage data L1 may be calculated based on the current value in the processing process. That is, the early-stage data L1 may not be detected in the teaching process.

The early-stage data L1 and the later-stage data L2 may partially overlap each other in time. For example, if each of the early-stage data L1 and the later-stage data L2 has a plurality of current values, the last current value of the later-stage data L2 need only be detected later in time than the last current value of the early-stage data L1.

The monitoring range ΔD may be set (S8 of FIG. 3) in every cycle A. That is, the monitoring range ΔD may be set between the peak hold step (S5 of FIG. 3) and the subsequent first sampling step (S3, S4 of FIG. 3). The peak hold step (S5 of FIG. 3) may not be performed in every cycle A. The peak hold step may be performed after 10 cycles A are completed.

The number of cycles A in the teaching process and the processing process, the teaching offset amount "h" in the peak hold step, and the offset amount H in the monitoring range setting step are not particularly limited. The number of processing parts in a single cycle (single workpiece W) is not particularly limited. These values can be input and updated as appropriate by the operator.

In the above embodiment, the "Yes" button 230, the "No" button 231, and the "Cancel" button 232 are displayed on the screen 23, as shown in S26 of FIG. 4. However, only the "Yes" button 230 and the "No" button 231 may be displayed on the screen 23. In this case, the "Yes" button 230 also serves as the "Cancel" button 232. This can reduce the number of buttons on the screen 23.

In the above embodiment, the control device 22 shown in FIG. 2 stops the lathe 1 when the current value is out of the monitoring range Δd. However, the control device 22 may stop the lathe 1 after the actual processing step A2 is finished. The control device 22 in FIG. 2 may not be contained in the lathe 1, and may be an externally connectable computer, etc.

In the above embodiment, the monitoring range ΔD is set in the teaching process, as shown in S8 of FIG. 3. However, the monitoring range ΔD may be set in advance before the lathe 1 is started. For example, the set monitoring range ΔD may be stored in advance in the storage section 220a in FIG. 2 before the lathe 1 is started.

In the above embodiment, the monitoring range ΔD is updated in the processing process, as shown in S21 to S26 of FIG. 4. However, the monitoring range ΔD may not be updated. That is, the monitoring range ΔD may be changed only by the correction shown in S14 of FIG. 3. The monitoring period ΔP shown in S9 of FIG. 3 may not be set.

The tool abnormality determination system of the present invention can be used for determination of abnormalities of various machine tools such as a tool of a milling machine, a drill of a drill press, etc.

What is claimed is:

1. A tool abnormality determination system for detecting abnormalities in a tool according to a state of the tool, by automatically and continuously performing correction of a monitoring range for detecting the abnormalities, the tool abnormality determination system comprising:
   a processor;
   a display; and
   at least one motor drive circuit connected to a respective at least one motor, the at least one motor drive circuit driving the at least one motor so as to process work by a tool on a workpiece, wherein
   the processor is configured to:
   set an offset amount;
   detect load data of the at least one motor at predetermined intervals; and
   use the load data of at least one of $1^{st}$ to $(M-1)^{th}$ cycles to correct a monitoring range for a load on the tool in an $M^{th}$ cycle (where M is an integer of 2 or more),
   the monitoring range is a difference between: (i) a first current value, which is an upper limit threshold at a given time in a first cycle; and (ii) a second current value, which is a lower limit threshold at the given time in a second cycle, the first current value and the second current value being peak current values, the lower limit threshold is determined by using the offset amount to correct a low load-side peak hold value, and the upper limit threshold is determined by using the offset amount to correct a high load-side peak hold value, processing the work on the workpiece by using the tool corresponds to a single cycle, the load data is an indicator of the load on the tool in the single cycle, the load data includes a plurality of current values, when a current value, of the plurality of current values, is out of the monitoring range, the processor is further configured to count a number of consecutive times the current value is out of the monitoring range, when the number of consecutive times does not exceed a number-of-consecutive-times threshold, the processor is further configured to continue to monitor the current value, and when the number of consecutive times exceeds the number-of-consecutive-times threshold, the processor is further configured to stop processing the work on the workpiece as soon as the current value is out of the monitoring range and display guidance on the display, the guidance prompting a user to confirm whether or not the tool is actually in an abnormal state.

2. The tool abnormality determination system according to claim 1, wherein the processor is further configured to:

perform an air-cut step of moving the tool so as to bring the tool into contact with the workpiece; and perform an actual processing step of processing the workpiece by using the tool, wherein the air-cut step and the actual processing step are performed during the cycle, and the actual processing step is performed after the air-cut step, wherein a plurality of pieces of the load data which are detected in or before the air-cut step in the $M^{th}$ cycle have early-stage data including at least one piece of the load data, and later-stage data including at least one piece of the load data which is detected later than the load data detected last in the early-stage data, and wherein the processor is further configured to:

use a load ratio between the early-stage data and the later-stage data to correct the monitoring range in the actual processing step of the $M^{th}$ cycle.

3. The tool abnormality determination system according to claim 2, wherein the processor is further configured to:

perform a teaching process which includes at least one of the cycles, and setting the monitoring range by using the load data detected in the at least one of the cycles; and perform a processing process which includes at least one of the cycles, and processing the workpiece while monitoring the load on the tool by using the monitoring range, and wherein the early-stage data is detected in the cycle of the teaching process.

4. The tool abnormality determination system according to claim 3, wherein the processor is further configured to:

perform the air-cut step in the cycle of the teaching process, the air-cut step performed in the cycle of the teaching process being a first air-cut step;

detect the early-stage data in the first air-cut step;

perform the air-cut step in the cycle of the processing process, the air-cut step performed in the cycle of the processing process being a second air-cut step; and detect the later-stage data in the second air-cut step.

5. The tool abnormality determination system according to claim 3, wherein the processor is further configured to:

perform the actual processing step in the cycle of the teaching process, the actual processing step performed in the cycle of the teaching process being a first actual processing step;

detect the early-stage data in the first actual processing step;

perform the actual processing step in the cycle of the processing process, the actual processing step performed in the cycle of the processing process being a second actual processing step; and detect the later-stage data in the second actual processing step in the cycle of the processing process.

6. The tool abnormality determination system according to claim 5, wherein the processor is further configured to:

detect the later-stage data in the actual processing step in the $(M-1)^{th}$ cycle.

7. The tool abnormality determination system according to claim 5, wherein the processor further configured to:

detect the later-stage data in the actual processing steps in a plurality of the cycles including the $(M-1)^{th}$ cycle.

* * * * *